United States Patent [19]
Chen et al.

[11] Patent Number: 5,990,486
[45] Date of Patent: Nov. 23, 1999

[54] APPARATUS AND METHOD FOR MEASURING COMPONENTS OF A SOLUTE STREAM

[75] Inventors: Eric B. Chen, Billerica; Chien-Chung Chen, Dracut; Alfred A. Donatelli, Medford; Antonio Morales, Somerville; Jason Barrett; William W. Bannister, both of Chelmsford, all of Mass.

[73] Assignee: University of Massachusetts, Boston, Mass.

[21] Appl. No.: 08/976,061

[22] Filed: Nov. 21, 1997

[51] Int. Cl.$^6$ .................................................. G01N 15/06
[52] U.S. Cl. ............................................ 250/573; 356/442
[58] Field of Search .................................. 250/574, 573, 250/339.12; 356/442, 441, 340, 338, 339

[56] References Cited

U.S. PATENT DOCUMENTS

| | | | |
|---|---|---|---|
| 4,329,986 | 5/1982 | Babb | 128/214 R |
| 4,528,178 | 7/1985 | Babb | 424/7.1 |
| 4,805,623 | 2/1989 | Jobsis | 250/339.12 |
| 4,950,908 | 8/1990 | Oblad et al. | 250/574 |
| 5,378,635 | 1/1995 | Yasuda et al. | 436/111 |
| 5,603,735 | 2/1997 | Zimin, Sr. et al. | 8/617 |
| 5,879,629 | 3/1999 | Capuano et al. | 250/339.12 |

FOREIGN PATENT DOCUMENTS

| | | |
|---|---|---|
| WO 91/18006 | 11/1991 | WIPO . |
| WO 92/01115 | 1/1992 | WIPO . |

OTHER PUBLICATIONS

Gill, "New Developments in Chemiluminescence Research", *Aldrichimica Acta*, vol. 16, No. 3, 1983, pp. 59–61 (Month Unknown).

Morton Dyes brochure, Technical Information, Aquamate®—Water Reducible Dyes, Jun. 1, 1996.

Baldwin, ARFF News, "Crash Fire Rescue Truck Dye–Water AFFF System Test Kit", vol. 8, No. 4, pp. 10–11 Jul./Aug., 1997.

*Primary Examiner*—Que T. Le
*Attorney, Agent, or Firm*—Fish & Richardson P.C.

[57] ABSTRACT

The invention features an apparatus and method for determining and controlling the concentration of a solute in a solute stream by measuring the concentration of an indicator agent.

19 Claims, 1 Drawing Sheet

APPARATUS AND METHOD FOR MEASURING COMPONENTS OF A SOLUTE STREAM

BACKGROUND OF THE INVENTION

This invention relates to a method of measuring the concentration of a solute in a solute stream.

The concentration of a solute component of a liquid can be difficult to monitor when the solute lacks an easily measurable property. For example, the addition of high molecular weight poly(ethylene oxide) ($[-OCH_2CH_2-]$) (POLYOX™) to turbulent water systems has been reported to enhance stream properties by reducing frictional drag and increasing volumetric flow rate. However, it is difficult to directly monitor the POLYOX™ concentration, e.g., in a flowing stream of water. Similarly, it is difficult to detect the concentration of aqueous film forming formulation (AFFF), an agent used to combat aviation fires, and other solutes.

One method of determining solute concentration involves the use of indicators with a high refractive index, such as diethylene glycol butyl ether (DBGE), that are mixed with the solute component. The concentration of the solute component can be determined by determining the refractive index of the solute stream. However, these indicators can be expensive and environmentally undesirable, and large amounts of such indicators, e.g., 20% (vol/vol) of DBGE in an AFFF solution, are typically added to the solute stream.

SUMMARY OF THE INVENTION

The invention is based on the discovery that when small amounts of non-toxic indicator agents are added along with a solute to liquid streams, the agents can be used to determine the concentration of the solute. Accordingly, the invention provides a method of measuring the concentration of a solute by following the concentration of an indicator agent that is easily identified. Also provided is an apparatus for adjusting the concentration of a solute based on the measured concentration of an indicator agent.

In one aspect, the invention features a method of monitoring the amount of solute added to a liquid stream by introducing a solute stream, which contains in a known ratio the solute and an indicator agent, into the liquid stream, subjecting at least a portion of the liquid stream to radiation; measuring an optical parameter of the indicator agent to determine the concentration of the indicator agent in the stream liquid; and determining the concentration of the solute in the liquid stream, based upon the concentration of the indicator agent in the liquid stream.

The indicator agent can include, e.g., fluorescein or a fluorescein salt, rubrene, or Rhodamine B. The solute can include, e.g., poly(ethylene) oxide or aqueous film forming formulation.

In some embodiments, the known ratio of the spectroscopic indicator agent to the solute in the solute stream is selected to result in an indicator agent concentration in the liquid stream of up to 100 ppm.

The method can optionally further include controlling the concentration of the solute in the liquid stream at a desired concentration by (e) comparing the desired concentration of the solute with the determined concentration of the solute in the liquid stream, (f) adjusting the amount of the solute stream introduced into the liquid stream to increase or decrease as needed to obtain the desired concentration of the solute in the liquid stream, (g) obtaining a next determined concentration of the solute in the liquid stream, (h) comparing the desired concentration of the solute in the liquid stream with the next determined concentration of the solute in the liquid stream, and repeating steps (b) through (d) as needed to maintain the desired concentration of the solute in the liquid stream.

In another aspect, the invention features an apparatus for regulating the concentration of a solute in a fluid stream. The apparatus can include: (a) a metering pump for introducing a mixture of a solute and an indicator agent into the fluid stream; (b) a detector for measuring the concentration of the indicator, wherein the detector is disposed in the fluid stream at a point downstream from the metering pump, and wherein the detector transmits the measured concentration of the indicator to the metering pump, and wherein the metering pump adjusts the amount of solute and indicator introduced into the fluid stream according to the measured concentration of the indicator.

The apparatus may optionally include a light source or a mixing chamber for mixing the solute and indicator compound.

The invention offers many advantages. The indicator agents used in this detection method are non-toxic, highly efficient, and economical. Additionally, this detection method can be used in a range of both aqueous and non-aqueous manufacturing operations in which the accurate blending of the solute is critical, such as in the blending of petroleum products or the addition of plasticizing agents to polymers. A further advantage of the invention is that the indicator agents provide greatly increased visibility for the fluid streams in which they are introduced, e.g., enhanced visibility of hose stream water in nighttime or other dark situation firefighting applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
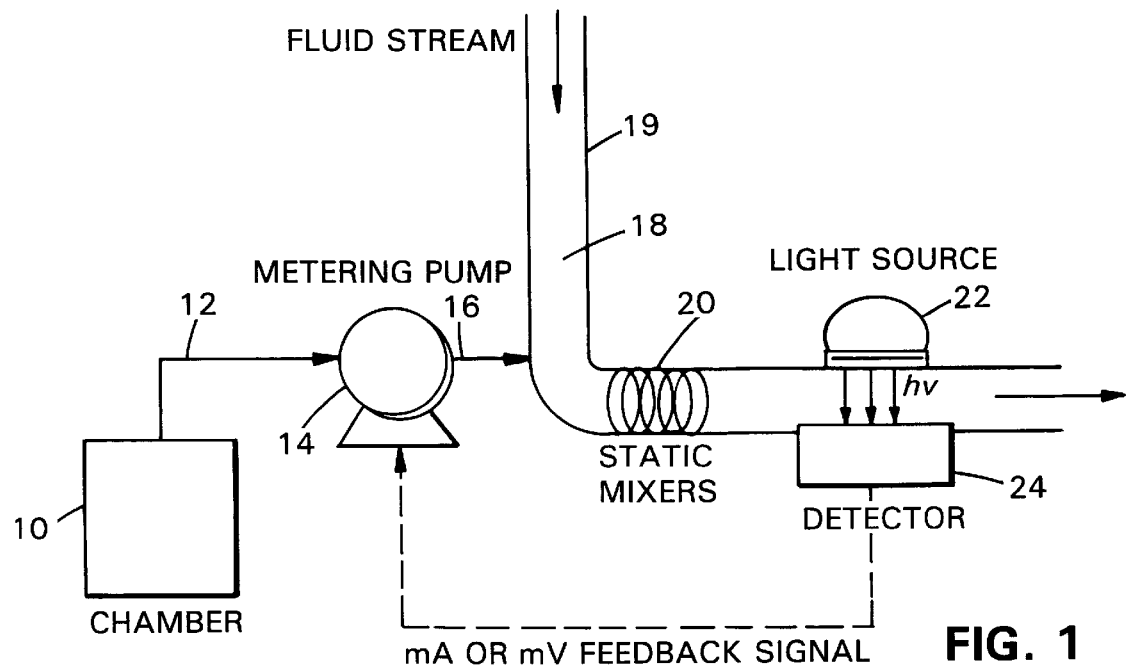
FIG. 1 is a schematic diagram of a feedback control system for adjusting the concentration of a solute system based on the concentration of an indicator agent.

The invention provides a method and apparatus for simply, accurately, and reliably monitoring solutes in aqueous and non-aqueous fluid streams by adding small amounts of an indicator agent to the solute, and then adding the indicator agent/solute mixture to the fluid stream. The invention additionally provides an apparatus for measuring the level of the solute in the fluid stream by measuring the emitted radiation of the indicator agent.

Method of Measuring Solutes in a Fluid Stream

The indicator agent and solute are mixed at a predetermined ratio, e.g., at 1:50, 1:100, 1:250, 1:500, 1:1000, or 1:2000 (mass/volume) so that the final concentration of indicator to the concentrated solution of solute is, e.g., 0.001–2%, 0.02–2.0%, 0.05–1.0%, or 0.15–0.3%, or about 0.2% (mass to volume) of indicator agent and solute. The indicator agent/solute mixture is then introduced into a fluid stream.

Once the indicator agent and solute are in the fluid stream, the concentration of the indicator agent can be determined and the amount of solute present can be simply determined. Light capable of detecting the indicator agent, e.g., incandescent or ultraviolet light, can illuminate the liquid at a predetermined reference point, e.g., at the nozzle of a hose stream carrying the liquid. The emitted light is measured and is proportional to the total indicator agent concentration. Because the ratio of the indicator agent and solute is known, the indicator agent concentration, in turn, can be used to determine the concentration of the solute.

In another aspect of the invention, the indicator agent can be a water insoluble dye that is dispersed in water solutions with a solute that is desired to be metered into a water stream. The intensity of coloration, which can be measured with a calorimeter, of the resulting feed stream due to the indicator agent represents the concentration of the solute. In addition, several such solutes, each containing a known concentration of a different water insoluble dispersed agent, can be measured at the same time. For example, a yellow dye and a red dye can mix in the feed stream to form orange color of different hues, depending on the ratio of the yellow to red agent. The resulting wavelengths would be indicative of the precise ratio.

The addition of indicator agents to aqueous and non-aqueous systems is a facile and accurate means of controlling the concentrations of other solutes (e.g., lubricants, surfactants, emulsifiers, dispersants or defoamers), and provides a fast, accurate and automatic method of determining the concentration of a solute. The method is particularly suitable for detecting solutes which themselves lack easily measurable properties, e.g., the firefighting hose stream additives POLYOX™ and aviation film forming formulation (AFFF).

In addition to measuring solutes useful in fire fighting applications, the new detection method can be applied to any manufacturing process in which an accurate measure of a soluble agent (e.g., lubricants, surfactants, emulsifiers, thickeners, dispersants, or defoamers) in the process is desirable. Examples of processes in which soluble agents are added to liquids include blending of gasolines, plasticizer addition in polymer formulation, or formulation of household cleaners, textile processing, industrial suspensions, paint strippers, and polishing fluids.

Apparatus for Measuring Levels of a Solute in a Stream Flow

FIG. 1 shows an apparatus for measuring the levels of solute in a stream flow. A indicator agent and solute are mixed in a chamber 10 and fed through a line 12 to a metering pump 14. The resulting indicator agent/solute mixture exits the metering pump 14 through an outlet line 16 and is fed into the fluid stream 18 in conduit 19. The fluid stream 18 containing the fluorescent agent optionally passes through one or more static mixers 20 and continues past a light source 22 located on one side of the fluid stream 18. A detector 24 is located on the opposite side of light source 22 to measure the signal emitted by the indicator agent upon illumination by the light source. The signal corresponding to the concentration of the indicator agent generated by the detector 24 is transmitted to the metering pump 14, which increases or decreases the amount of delivered solute according to the transmitted signal.

The static mixers 20 facilitate the mixing of an agent in a water hose stream and can be obtained from engineering supply houses. The photo detector 24 can be a conventional photo light meter. The light source 22 can be an incandescent light bulb, or a small UV light source.

Indicator Agents

The indicator agent can be any substance that can be detected spectroscopically or visually, e.g., in the ultraviolet or visible light range. Indicator agents can be either water soluble or water insoluble. Water soluble indicator agents include rhodamine B and fluorescein salts. The pH of the solution containing the fluorescein salt should be at least slightly basic.

Other suitable indicator agents include "whitening agents" (such as UVITEX-OB (Ciba-Geigy)), rosamine, napthylsulfonic acids, and a number of coumarin dyes. Water insoluble fluorescent agents include 131-SC and FGSC (Morton Chemical). The indicator agent may in addition be composed of one or more substances.

Fluorescein salts are particularly suitable for use as indicator agents because they absorb light at the 492 nm wavelength (high UV range) and emit at a wavelength of 515 nm, which is in the visible range. Fluorescein is also cheap, non-toxic, and degrades quickly and completely.

The disodium salt of fluorescein is dissolved in water at a pH of about 10 to 11. At this pH, fluorescein salts are highly fluorescent upon illumination with visible (blue) or near ultraviolet light, emitting a vivid yellow-green fluorescent color. As an added benefit, illuminating a fluorescein-treated water stream with, for example, UV light, produces a yellow-green fluorescent glow to aid in nighttime firefighting.

Non-aqueous agents can include Morton's Fluorescent Yellow 131 (Morton Chemical Company, Chicago), and rubrene (Aldrich Chemical Co). Water-insoluble dyes are discussed in Zimin et al., U.S. Pat. No. 5,603,735, and can include any pigments commonly used in water color formulations. Examples include AQUAMATE™ (Morton International).

Adding and Measuring the Indicator Agent

The indicator agent, e.g., fluorescein disodium salt or another dye, is added to a concentrated solution of the solute at a low concentration, and the mixture is placed in a reservoir. The indicator agent and the solute can optionally be mixed as solids prior to being added to a liquid.

The indicator agent/solute mixture can then be dispensed into a fluid stream using methods known in the art. For example, an indicator agent mixed with a solute, e.g., POLYOX™, can be pumped from the reservoir with a positive displacement variable speed gear measuring pump into a fire hose stream (at the pumper truck or at the hydrant). An in-line spiral static mixer can be placed in a hose section to be coupled with the fire hose just beyond this point of admixture to enhance the mixing of the indicator agent/solute mixture into the hose stream as it traverses the hose to the nozzle.

Figure 2:
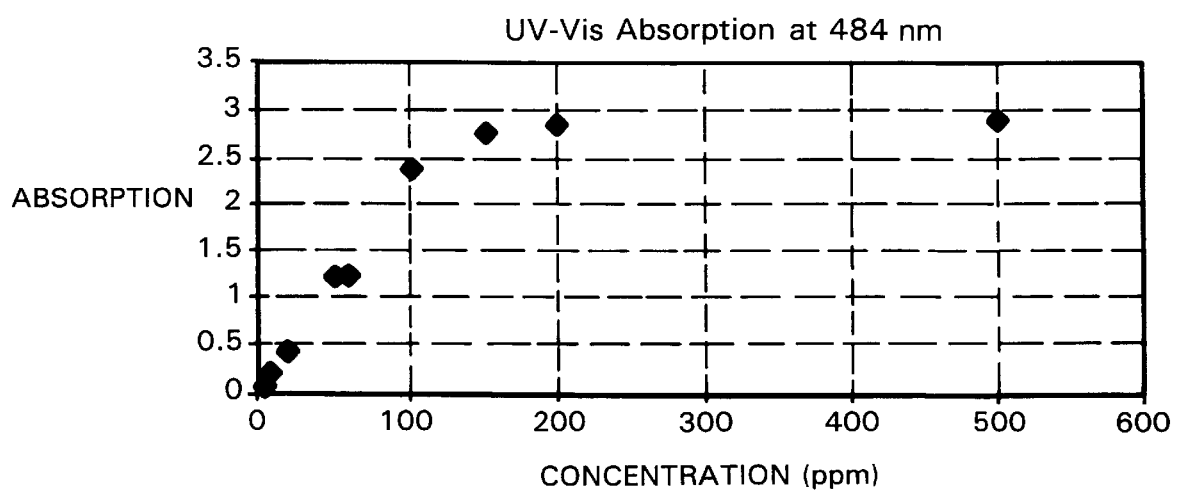
FIG. 2 is a graph showing the relative absorption at 484 nm as a function of fluorescein concentration.

The final concentration of the indicator agents in the liquid stream can be about 10000 ppm to 1 ppm, or about 1000 ppm to 1 ppm, or about 100 ppm to 1 ppm, e.g., about 10 ppm when fluorescein is used to detect a solute. The actual concentration to be used in a given application depends on the ultimate concentration to be achieved in the liquid stream. The amount of indicator agent (and thus also of the solute) can be determined by measuring the intensity of the emitted light, e.g., the fluorescent light intensity in the case of a fluorescein indicator agent. An example of the relative absorption at 484 nm of varying concentrations of fluorescein is shown in FIG. 2.

Thus, by measuring the intensity of the emitted fluorescence, and knowing the ratio of indicator agent to solute, the solute concentration can easily be determined using a small, cheap and readily available photo light meter as is commonly used by amateur and professional photographers.

At the intended low indicator agent concentrations in the solute stream, there is a linear relationship between concentration and fluorescent intensity. Thus, a light meter would be calibrated to indicate a given intensity reading for a known fluorescent agent concentration. The concentration of an unknown solution can be determined accordingly.

The concentration of the indicator agent can also be monitored and used to adjust upward or downward the amount of the measured solute by using an apparatus such as that shown in FIG. 1. To monitor the amount of fluorescent dye (and thus, by extension, the amount of the specific, known solutes) in the liquid stream, e.g., in a fire hose, a small battery operated light illuminating in the near-ultraviolet range can be placed either in-line (within the hose) or out-of-line (using a low pressure feed diverted from the hose) just prior to the nozzle. To measure the intensity of fluorescent light after it passes through the fluid stream, a photoelectric light meter is placed opposite to the light source. The photoelectric signal generated from the light meter can be converted into milliamp or millivolt signals. These signals are then input into an ammeter or voltmeter with controlling circuitry to operate metering controls at the gear pump. The readings of the voltmeter or ammeter provide the basis for manual control of the gear pump, with excessively high readings being the basis for reduced levels of indicator agent input, and lower than desired readings being the basis for increased indicator agent input.

Suitable Fluid Systems in Which Solute Levels Can Be Measured

Indicator agents can be used to monitor solute systems in a variety of fluid systems, e.g., as a way to monitor concentrations of additives in firefighting streams, blending various grades of gasoline in a vending pump, or as monitoring liquid components of a food composition.

The invention will be further described in the following examples, which do not limit the scope of the invention described in the claims.

EXAMPLES

Example 1

Derivation of a Calibration Curve for the Determination of Fluorescein Concentration in an Aqueous Solution The purpose of this experiment was to relate emitted fluorescence to the concentration of fluorescein in the solution. The fluorescein concentration, in turn, could be used to determine the amount of POLYOX™ present in a POLYOX™/fluorescein solution containing POLYOX™ in a known amount relative to fluorescein.

A master batch solution of POLYOX™/fluorescein aqueous solution at a relative ratio of 7.5 (mass/mass) was prepared by mixing 60 grams of POLYOX, 8 grams of fluorescein, and 0.6 grams of sodium hydroxide in 3750 ml of water. The master batch solution was then diluted with water to obtain different fluorescein aqueous solutions with concentrations ranging from 0 ppm to 500 ppm.

A GBC UV-VIS 916 spectrophotometer was used to provide fluorescent illumination and to determine resulting fluorescent intensities.

Three major UV-VIS absorption peaks were observed at 484, 320, 237 nm. Because 484 nm is in the visible light range, absorption at this wavelength was chosen for further study. Light absorption increased linearly as fluorescein concentrations increased from 0 up to 140 ppm. Absorption did not increase with further increases in fluorescein concentration.

In the linear range, the concentration of fluorescein can be accurately determined by the equation:

$$X = 50.5(Y) + 2.32$$

Where Y is the absorption intensity and X is the concentration of fluorescein.

Because the POLYOX™ and fluorescein components were mixed at a relative ratio of 7.5 (mass/mass), the concentration of POLYOX was then determined by the following formula:

$$[POLYOX] = 7.5(X)$$

For example, if the absorption intensity is 1.8, the concentration of fluorescein will be 93 ppm, and the POLYOX concentration will be 700 ppm.

Example 2

Use of Fluorescein To Meter Poly(ethylene oxide) Levels in a Fluid Stream

The addition of minute amounts of poly(ethylene oxide) (POLYOX™, WSR Coagulant, Union Carbide) with a molecular weight of $6 \times 10^6$ g/Mol) to a water stream has previously been demonstrated to improve flow properties for firefighting applications; however, directly measuring the level of PCLYOX™ present in the hose stream is difficult. To overcome this problem, a 1% POLYOX™ solution was formulated with a fluorescein indicator agent (0.20% of a 70% solution of the fluorescein sodium salt) and 0.02% sodium hydroxide. The purpose of the fluorescein was to accurately determine the concentration of poly(ethylene oxide) present in the fire hose during discharge. The fluorescein provided a fluorescent green color at pH levels greater than 9.0.

The POLYOX™/fluorescein mixture was introduced into a 500 gallon holding tank of a fire engine equipped with a 2,000 gpm centrifugal pump. No complex blending equipment was used.

Each incremental increase in poly(ethylene oxide) concentration was created by adding five gallons of the 1% POLYOX™ solution to the holding tank. The solution was circulated for thirty seconds in the holding tank to form a homogenous mixture. Treated and untreated water was pumped at a pressure of 250 psi through 500 feet of standard 1¾ inch hose. The discharge nozzle of the hose was set at a fixed angle, 30° with the horizontal. Each test lasted approximately two minutes, releasing about 75% of the total volume of the fire engine reservoir. For each experimental run, discharge flow, nozzle pressure, and stream reach were monitored after sixty seconds from the start of the stream discharge.

Samples from each test were characterized for fluorescein concentration by UV-VIS spectrophotometry (Spectronic 20D, Milton Roy) wavelengths of 480–495 nm. By multiplying the measured fluorescein concentration by the ratio of POLYOX™ to fluorescein, this technique ultimately determined the concentration of POLYOX™ in the hose stream for each test.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of monitoring the amount of solute added to a liquid stream, the method comprising:
   a) introducing a solute stream into said liquid stream, said solute stream comprising, in known ratio, the solute and an indicator agent;
   b) subjecting at least a portion of said liquid stream to radiation;
   c) measuring an optical parameter of said indicator agent in the liquid stream to determine the concentration of said indicator agent; and
   d) determining the concentration of said solute in said liquid stream, based upon the concentration of said indicator agent in said liquid stream.

2. A method of claim 1, wherein said indicator agent comprises fluorescein or a salt thereof.

3. A method of claim 1, wherein said solute comprises poly(ethylene) oxide.

4. A method of claim 1, wherein the known ratio of said spectroscopic indicator agent to said solute in said solute stream is selected to result in an indicator agent concentration in the liquid stream of up to 100 ppm.

5. A method of claim 1, wherein said solute comprises an aqueous film forming formulation.

6. A method of claim 1, wherein said indicator agent comprises rubrene.

7. A method of claim 1, wherein said indicator agent comprises Rhodamine B.

8. A method of claim 1, further comprising controlling the concentration of the solute in the liquid stream at a desired concentration by
   e) comparing the desired concentration of the solute with the concentration of the solute determined in step d) in the liquid stream;
   f) adjusting the amount of said solute stream introduced into said liquid stream to increase or decrease the amount of said solute stream as needed to obtain said desired concentration of the solute in the liquid stream;
   g) repeating steps b) through d) to a new concentration of the solute in the liquid stream;
   h) comparing the desired concentration of the solute in the liquid stream with the new concentration of the solute in the liquid stream; and
   i) repeating steps b) through d) as needed to maintain the desired concentration of the solute in said liquid stream.

9. A method of claim 8, wherein said indicator agent comprises fluorescein or a salt thereof.

10. A method of claim 8, wherein said solute comprises poly(ethylene) oxide.

11. A method of claim 8, wherein said known ratio of said indicator agent to said solute in said solute stream is selected to result in an indicator agent concentration in the liquid stream of up to 100 ppm.

12. A method of claim 8, wherein said solute comprises an aqueous film forming foam.

13. A method of claim 8, wherein said indicator agent comprises rubrene.

14. A method of claim 8, wherein said indicator comprises Rhodamine B.

15. The method of claim 1, wherein said optical parameter is emitted radiation.

16. The method of claim 15, wherein said radiation is fluorescent radiation.

17. An apparatus for regulating the concentration of a solute in a fluid stream, the apparatus comprising:
   a) a metering pump for introducing a mixture of a solute and an indicator agent into the fluid stream;
   b) a detector for measuring the concentration of said indicator agent, wherein said detector samples the fluid stream at a point downstream from said metering pump, wherein said detector transmits a signal corresponding to the measured concentration of the indicator agent to said metering pump, and wherein said metering pump adjusts the amount of solute and indicator agent introduced into said fluid stream according to the measured concentration of the indicator agent.

18. The apparatus of claim 17, further comprising a light source.

19. The apparatus of claim 17, further comprising a mixing chamber for mixing the solute and indicator agent.

* * * * *